(12) United States Patent
Jacob et al.

(10) Patent No.: US 7,691,438 B2
(45) Date of Patent: Apr. 6, 2010

(54) ENZYME GRANULATE PRODUCTION METHOD AND RESULTING ENZYME GRANULATES

(75) Inventors: Michael Jacob, Weimar (DE); Karlheinz Rümpler, Weimar (DE); Mike Waskow, Weimar (DE)

(73) Assignee: Glatt Ingenieurtechnik GmbH, Weimar (DE)

( * ) Notice: Subject to any disclaimer, the term of this patent is extended or adjusted under 35 U.S.C. 154(b) by 1371 days.

(21) Appl. No.: 10/862,238

(22) Filed: Jun. 7, 2004

(65) Prior Publication Data

US 2006/0088923 A1    Apr. 27, 2006

Related U.S. Application Data

(63) Continuation-in-part of application No. 10/739,845, filed on Dec. 18, 2003, now abandoned.

(30) Foreign Application Priority Data

| Jun. 11, 2003 | (DE) | ................. 103 26 231 |
| Dec. 9, 2003 | (DE) | ................. 103 57 827 |
| Jan. 27, 2004 | (DE) | ................. 10 2004 004 202 |
| Feb. 19, 2004 | (DE) | ................. 10 2004 008 020 |

(51) Int. Cl.
*B05D 7/00* (2006.01)
(52) U.S. Cl. ...................... 427/212; 427/213
(58) Field of Classification Search ................ 427/212, 427/213; 435/187
See application file for complete search history.

(56) References Cited

U.S. PATENT DOCUMENTS

| 3,443,621 A | 5/1969 | Dubreuil |
| 4,009,076 A | 2/1977 | Green et al. |
| 4,100,263 A | 7/1978 | Miller |
| 4,233,007 A | 11/1980 | Karlsson |
| 4,354,450 A * | 10/1982 | Nagahama et al. .......... 118/303 |
| 4,736,895 A | 4/1988 | Hüttlin |
| 4,858,552 A | 8/1989 | Glatt et al. |
| 4,876,198 A | 10/1989 | Markussen |
| 4,946,654 A | 8/1990 | Uhlemann et al. |

(Continued)

FOREIGN PATENT DOCUMENTS

CA    2 372 441    11/2000

(Continued)

*Primary Examiner*—Roberts Culbert
(74) *Attorney, Agent, or Firm*—Volpe and Koenig, P.C.

(57) ABSTRACT

A method for producing enzyme granulates, the resulting enzyme granulates, and their use in formulations, e.g., for animal feed, food, washing means, rinsing means, and/or for pharmaceutical purposes and the like. The enzyme granulates show, in particular, a high relative percentage of active enzymes, certain grain sizes, good storage stability, especially small roundness factor, and/or low residual moisture percentage as well as preferably additional specific properties. According to the invention, the enzyme granulates are produced by linking the thermal conditions in the spray zone and the temperature conditions in the remaining region of the fluidized bed. In the process according to the invention, this is achieved in that the supply of heated processing gas is realized for drying exclusively in the injection region. The reliable supply of particles in the injection region is realized through the special geometrical shape of the apparatus under the use of gravity. Through the addition of inert particles as nuclei material for cores, the absolute content of enzyme activity of the enzyme granulate can be controlled.

17 Claims, 1 Drawing Sheet

U.S. PATENT DOCUMENTS

| | | | |
|---|---|---|---|
| 5,213,820 | A | 5/1993 | Uhlemann et al. |
| 6,579,365 | B1 | 6/2003 | Jones et al. |
| 6,740,632 | B1 | 5/2004 | Jacob et al. |
| 2003/0124224 | A1 | 7/2003 | Barendse et al. |
| 2003/0196598 | A1 | 10/2003 | Jones et al. |
| 2006/0105024 | A1 * | 5/2006 | Andela et al. ............... 424/442 |

FOREIGN PATENT DOCUMENTS

| | | |
|---|---|---|
| DE | 1 667 217 | 2/1974 |
| DE | 25 55 917 | 11/1976 |
| DE | 31 17 892 | 3/1982 |
| DE | 35 30 744 | 2/1989 |
| DE | 199 22 753 | 11/2000 |
| DE | 101 46 778 | 4/2003 |
| EP | 0332929 | 9/1989 |
| WO | WO 98/55599 | 12/1998 |
| WO | 0183727 A2 | 11/2001 |

* cited by examiner

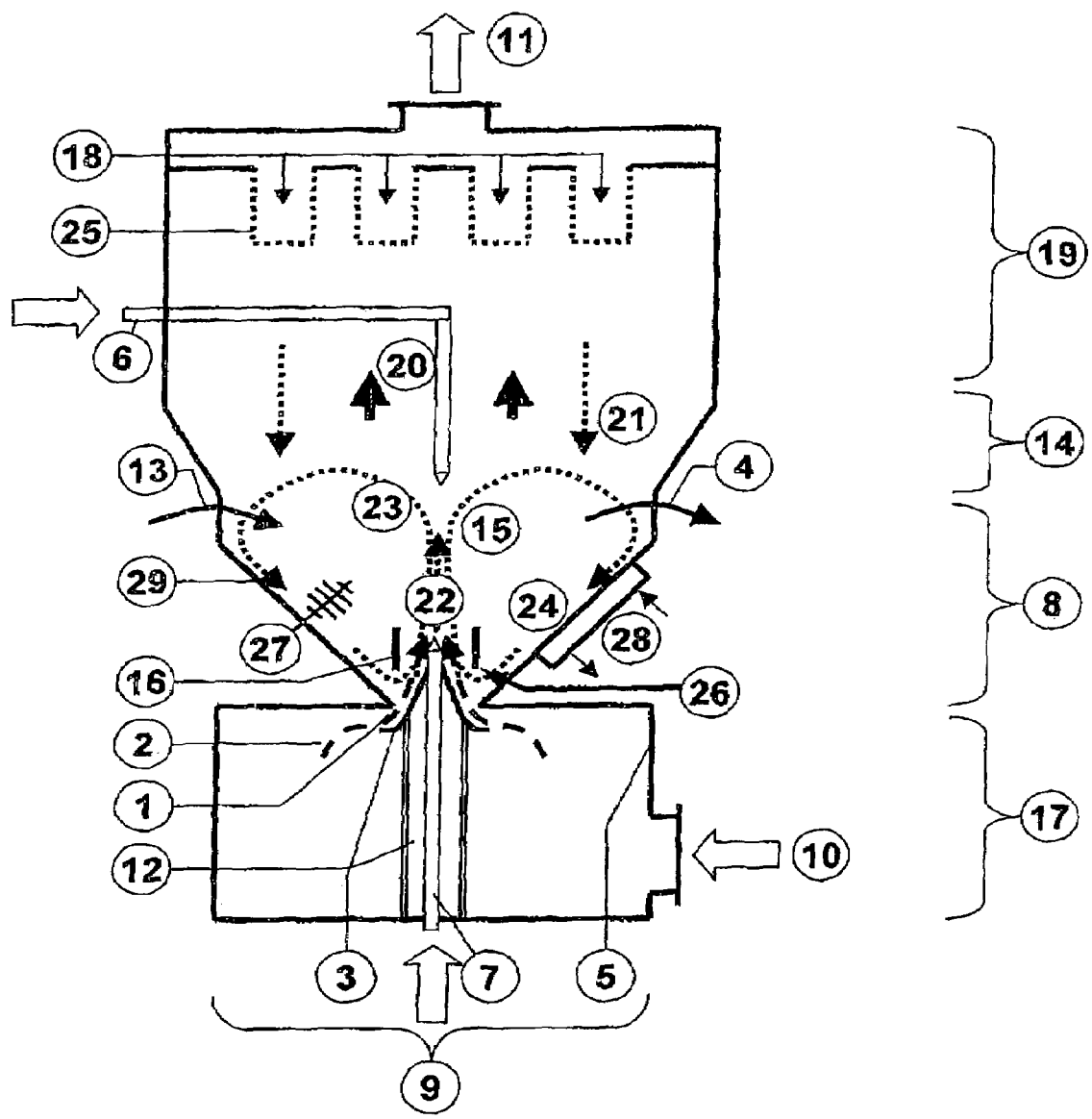

ENZYME GRANULATE PRODUCTION METHOD AND RESULTING ENZYME GRANULATES

CROSS-REFERENCE TO RELATED APPLICATIONS

This application is a continuation-in-part of U.S. application Ser. No. Ser. No. 10/739,845 (abandoned), filed Dec. 18, 2003, and also claims the benefit of priority from German Application Nos. 103 26 231.8, filed Jun. 11, 2003; 103 57 827.7, filed Dec. 9, 2003; 10 2004 004 202.0, filed Jan. 27, 2004; and 10 2004 008 020.8, filed Feb. 19, 2004, all of which are incorporated by reference herein as if fully set forth.

BACKGROUND

The invention relates to a method for producing enzyme granulates, the resulting enzyme granulates, and as well as their use for producing formulations containing these enzyme granulates, a method for producing enzyme granulates comprising inert materials.

Enzymes are being used in many branches of industry in ever greater capacities. This concerns both the produced amounts and also the wide range of enzyme forms. As a rule, enzymes are provided in liquid form or also as a dry substance. In recent years, granulates in commercial form are becoming ever more preferred by users or by the post-processing industry. These granulates distinguish themselves through advantageous properties, such as easy dosing, very good flow properties, homogenous inner structure, high particle density, low dust content, as well as a uniform and closed surface. Because enzymes can be characterized, as a rule, by their particular properties, such as instability, e.g., in an aqueous environment, and the creation of allergic reactions, the granulate form has been proven as an advantageous commercial form.

The stability of enzymes can be improved by transforming these into a dry form. This can be performed, e.g., through spray drying, various agglomeration processes (wet granulation in mixers or fluidized-bed agglomeration) or through build-up granulation in fluidized bed apparatuses (spray granulation).

Disadvantages for spray drying is that very large apparatus volumes are needed and the powdery product contains a considerable dust content.

In order to reduce this dust content, the spray drying is often performed by means of multi-stage drying systems. Disadvantages are that enzyme granulates produced with such a multi-stage drying system have a poor, i.e., high roundness factor (given by the ratio of the surface of a granule to the surface of a perfectly round granule) of more than 1.6. Due to the lower roundness and thus projecting sections that can easily break off, enzyme granulates with a roundness factor of 1.6 quickly lead to a high dust content under mechanical loading, such as during packing and transport, for example.

This dust content requires special protection measures for the production personnel and users as well as significantly greater expense in system equipment for dedusting, ventilation, and for reuse of the dust.

One possible method for producing enzyme granulates is represented by the build-up granulation in a fluidized bed, such as that published in WO 01/83727 A2. Here, a process is described, for which the liquid enzyme formulation is injected into a fluidized bed by means of spray nozzles. The dust resulting in the process is separated from the exhaust air and fed back to the granulation process as nuclei. The resulting granulates are removed from the process under the use of one or more gravity sifters mounted in the air distribution plate of the fluidized bed apparatus. The size of the discharged granulates can be adjusted by the amount of sifting gas. Optionally, the granulates can also be coated. The method uses the fluidized bed process from EP-A-0163836 and EP-A-0332929.

The described fluidized bed process is distinguished in that for uniform distribution of the processing gas needed for fluidization and drying, an air distribution plate is mounted over the entire cross section of the fluidized bed apparatus. The spray nozzles used for injecting the liquid spray vertically upwards and are integrated directly in the air distribution plate (EP-A-0332929) or are encompassed by a sifter at the height of the air distribution plate (EP-A-0163836). The granulation nuclei required for the process are produced partially through spray drying of the injected liquid on the fluidized bed material through partial uncovering (through spraying) of the spray nozzles. The fluidized bed mass is formed by a state of equilibrium between the spray-dried nuclei and the fine particles supplied by the separating process, as well as the granulate discharge. There is no separation of granulates that are too large.

Due to the injection of liquid, the particles contained in the fluidized bed are wetted with the liquid in the injected region and the liquid film is dried on the particle surface. In the remaining region of the fluidized bed, no drying of the particles with essentially wetted surfaces takes place outside of the nozzles. Instead, only a small portion of the moisture contained in the pores of the particles is evaporated, which leads to an increase of the (average) particle temperature. However, in conventional fluidized beds, a supply of heated processing gases is also necessary outside of the spray region of the nozzles in order to mix the particles in the apparatus and to constantly supply particles into the spraying region. Because the production of enzymes is sensitive to temperature, with these known methods, an optimum yield of enzyme activity cannot be achieved (low relative activity relative to the original enzyme activity, i.e., in addition to active enzyme, too large a percentage of inactive or destroyed enzyme is present, which means that for the same amount of total activity [absolute activity], more enzyme must be used). In addition, non-uniform temperature distributions in the conventional process cannot be prevented.

For this processing guide in the described systems, the residence time can only be decreased by not drying the granulates up to the necessary end value and/or producing an enzyme granulate of lower grain size, which, however, negatively effects the quality of the enzyme granulate. The enzyme granulates known from the state of the art have a high percentage of inactive carrier material and thus a low absolute activity, a high percentage of inactivated enzyme (low relative activity), a low value for the average grain size D50 (grain size, for which 50 wt % of the particles have a diameter that is smaller and 50 wt % of the particles have a diameter that is greater than the average grain size D50) or a high moisture content, or usually two or more of these properties.

For example, according to a method described in WO 01/83727 A2, a yield of enzyme activity of more than 85% (relative to the theoretically possible total enzyme activity) can be achieved only for small particles and/or a moisture content (residual humidity) of more than 5%.

On the other hand, WO 98/55599 A2 describes a method for producing enzyme granulates under the use of an extrusion device and a bonding apparatus for the use of a carrier material (such as corn starch). This method is also described in Example 2 of WO 01/83727.

Here, an enzyme activity yield of 95% (relative enzyme activity) and a granulate with an average grain size D50 of 600 µm, a moisture content of 5%, and a roundness factor of 1.4 are achieved. This method has the disadvantage that an enzyme apparatus with 27% dry substance starch must be mixed in a weight ratio of 1:2 in order to achieve an extrudable mixture. The enzyme granulate obtained through the extrusion process has an active enzyme material content of less than 13% (absolute enzyme activity) relative to the dry substance.

The enzyme granulate that can be achieved with the spray-drying method according to WO 01/83727 does produce granulate with a roundness factor in the preferred range of 1-1.6 and even particles of an average grain size D50 of 620 µm (see Table 2, Experiment 2), but the inactive carrier material content is much lower, wherein the content of total enzymes (active and inactivated) is higher than that for the processing product described in WO 98/55599. However, a disadvantage for the enzyme granulate according to WO 98/55599, which can also be inferred from the mentioned Example 2 in WO 01/83727, is that the relative percentage of active enzyme, relative to the total amount of active and inactive enzyme, is at 85% significantly lower than for the extrusion method.

According to the function described in WO 01/83727, the enzyme granulates are produced according to the method from EP 0 332 929. This method has the property that the bed contents adjust automatically (see EP 0 332 929, page 22, line 27). Therefore, for a certain granulation output, the residence time can no longer be controlled. Thus, in Example 1, the contents of the fluidized bed is 3 kg and the granulation output is at 1.5 kg/hour for granulation from an aqueous salt solution with contents of 23 wt % dry material. The residence time is thus fixed at 2 hours in this case. Thus, the residence time is determined by the ratio of bed content in kg to granulation output in kg/hour.

SUMMARY

The object of the invention is to create a method for producing enzyme granulates, especially with low dust content, for which the enzyme granulates can be produced in continuous or batch wise operation under the prevention as much as possible of non-uniform temperature distributions in the production process and with an increase of the yield of (relative) enzyme activity. Simultaneously, the controllability of the granulation should be improved for the production. In particular, the important object of the present invention is to create a granulation method, which enables a shorter residence time in comparison with the known fluidized bed methods under otherwise the same conditions, like composition of the enzyme concentrate, drying-air temperatures, average grain size D50 of the granulate, and roundness of the granulate. This object is achieved according to the invention, which in one preferred embodiment also provides an especially gentle method.

According to the invention, the production of enzyme granulates is performed by linking the thermal conditions in the spray zone and the temperature conditions in the remaining region of the apparatus. In particular, relative to the method from the state of the art, lower material residence times can be achieved, which leads to a higher relative enzyme activity in the enzyme granulates obtained by the method of a preferred embodiment of the invention. In the process according to a preferred embodiment of the invention, this is achieved because the supply of heated process gas for drying is realized mainly, i.e., particularly at more than 80%, preferably exclusively, in the injection region. The secure supply of particles into the injection region is realized in particular through the special geometrical shape of the apparatus under the use of gravity, but it can also happen pneumatically or through a combination of geometrical shape under the use of gravity and pneumatic supply.

The advantage of the solution according to the invention is provided in that the production conditions are adapted to the material properties to be produced. Non-uniform temperature distributions are prevented as much as possible, wherein also an increase of the output of enzyme granulates is achieved.

The object of the present invention is also to provide an enzyme granulate with low dust content and higher (relative) percentage of active enzyme than in the state of the art in combination with an average grain size D50 of 60 (especially 100 µm) to 2000 µm, good storage stability, especially a small roundness factor, and/or low moisture content. The enzyme granulates according to a preferred embodiment of the invention and obtained from the method according to the invention exhibit these advantageous properties. These can be advantageous for the production of many interesting formulations, in particular by adding one or more suitable carrier materials and/or compression into suitable application forms.

Additional advantageous configurations are described herein and are explained extensively in the description together with their effect.

The enzyme granulates that can be produced according to the invention are highly concentrated and water-soluble or water-dispersible and have an average grain size D50 of 60-2000 µm and are further characterized especially by a dust content of <800, preferably less than 500 ppm according to the Heubach test, at a ratio of active enzyme content to the sum of active and inactive contents (relative enzyme activity) of 80% or greater, especially 88% or more. The compression strength of the enzyme granulates that can be produced is preferably 10 MPa or higher, in one possible, preferred embodiment of the invention 20-50 MPa, and the bulk density is 500 µl or more, in one possible, preferred embodiment 550-850 g/l. The grain size distribution, characterized by the ratio $d_{10}/d_{90}$ (definition: $d_{10}$ is the grain diameter, at which 10% of the mass of the granulate is smaller than this diameter; $d_{90}$ is the grain diameter, at which 90% of the mass of the granulate is smaller than this diameter), is especially 0.4 or higher. The absolute phytase activity of an enzyme granulate that can be produced advantageously according to the invention (here containing phytase as an enzyme) is preferably equal to or greater than 15,000 FTU/g. Here, an FTU is the enzyme activity, which releases 1 micromole of phosphate per minute at 37° C. under assay conditions (0.25 M sodium acetate, pH value of 5.5; 51 nM sodium phytate).

BRIEF DESCRIPTION OF THE DRAWING

The invention is explained in more detail in the following with reference to a preferred embodiment. In the associated drawing, a system for performing the method according to the invention is shown schematically.

DETAILED DESCRIPTION OF THE PREFERRED EMBODIMENTS

The amount of heated processing gas 10 (usually heated air) needed for drying the enzyme granulate to be produced is fed to an inlet air chamber 17 with a rectangular cross section 9 and bordering side walls 5. In the inlet air chamber 17, the processing gas 10 spreads and enters through gap openings 1 in the form of gas streams 2 into the processing space 8. The processing gas stream, which preferably enters horizontally into the gap 1, is deflected by the deflection part 3 preferably upwards into the processing space 8 and flows as a type of free stream into the apparatus. Furthermore, the apparatus cross section can optionally enlarge in the expansion zone 14, so that the velocity of the processing gas flow constantly decreases upwards. The gas leaves the apparatus as exhaust gas 11 above the expansion zone 14 through the exhaust gas part 19, in which a dedusting system (e.g., filter cartridges or textile-filter elements) can be optionally integrated.

In the processing space 8, a certain amount of particles is entrained upwards in the processing gas stream. In the upper region of the processing space 8 as well as in the expansion zone 14 located above this space, the gas velocity decreases, so that the particles flowing upwards exit laterally from the gas stream 23 and fall back into the processing space 8. The processing space 8 is limited in the lower region by inclined side walls 29. Due to these inclined sides, the particles are fed under the effect of gravity by the return zone 24 in the direction of the gas inlet gap 1, where they are then entrained again by the processing gas and brought back into the processing space 8.

This mechanism forms a very large uniform solids circulation 15 consisting of an upwards flow and a return in the direction of the processing gas inlet. Therefore, even for very low amounts of particles in the processing space 8 in the core zone above the deflection part 3 there is a high particle density. In this region, one or more spray nozzles 7 are arranged, which spray upwards aligned with the processing gas stream and are used for feeding the liquid enzyme formulation.

Through the high particle load in the core zone, very advantageous conditions for the heat and material transfer are produced in the injection zone 22. Furthermore, it is achieved that the liquid is separated as much as possible from the particles and therefore this uniformly wets the particle surfaces. The uniform wetting with simultaneous high solids circulation between the injection region and return zone 24 has the effect that a very uniform liquid film is formed. Through the drying process, the liquid evaporates and leaves the apparatus with the exhaust gas 11. The solids obtained in the formulation remain on the particle surface. Therefore, the granulates grow very uniformly and homogeneously, which leads to a very narrow grain-size distribution. Through the circular-like solids stream formed in the processing space 8, a spray drying region and then a granulation region is formed in the region of the spray nozzles 7 and 6.

The processing gas can discharge a portion of the particles as well as fine material and dust from the processing space 8 as solids-bearing exhaust gas 20. For separating these particles, the filter system optionally integrated in the discharge part 19 or dedusting systems connected downstream of the apparatus can be used. In the case of an integrated dedusting system 25, e.g., compressed air pulses 18 can be used to feed the retained particles as separated solids 21 back into the processing space 8.

In comparison with fluidized bed apparatuses with integrated filter systems, the dust return is simplified in that the upwards directed processing gas stream is essentially locally limited and thus the returning particles can reliably sink outside of the gas stream. This mechanism is additionally supported by the suction effect in the vicinity of the gas inlet gap 1. Alternatively, particles separated from the exhaust gas or enzyme-bearing particles obtained in some other way (see below) are returned into the processing space 8. For this purpose, a wide range of feeds 26 is arranged in the lower region of the inclined side walls 29. Due to the high velocity of the processing gas stream in the vicinity of the gas inlet gap 1, the fine particles are suctioned and fed to the injection zone 22, where the particles are wetted with liquid and participate in the growth process.

Optionally installed baffle plates 16 support the gas stream, amplify the suction effect, and improve the supply of the solids into the injection zone 22. Possibly occurring agglomeration effects are minimized, because in the injection region there are very high flow velocities and thus higher separating forces than occur in fluidized beds. Therefore, particles are separated and grow into very sphere-like granulates.

The flow profile of the processing gas in the processing space 8 further has the effect that fine particles returned into the processing space from the optionally integrated filter system do not fall back into the injection zone 22. Therefore, the adhesion of fine particles and resulting agglomeration processes are stopped.

For continuous processing control, the apparatus can be equipped with various optional inlet systems 13 for solids. In this way, e.g., enzyme particles can be fed to the process, which, e.g., can be obtained through size reduction, e.g., of (too large) granulates, and/or consist of too small granulates or one or more enzyme particles or enzyme-bearing educts in the form of sufficiently fine dust and/or powder obtained in some other way. Such enzyme particles or enzyme-bearing educts (enzyme-bearing intermediate products) can be products of other processing stages and methods (e.g., spray drying of enzyme solutions). The percentage of these incoming enzyme-bearing intermediate products equals, in particular, 1 wt % or more, in one possible, preferred embodiment of the invention 5-20 wt %. Here, it is also possible and can be advantageous if the inlet enzyme particles are produced by a separate spray drying of an enzyme suspension. Here, it is also possible, in one possible, advantageous embodiment of the invention to supply enzyme particles already at the beginning. These particles are then used as granulation nuclei or as starter filling for shortening the startup time. In addition, here additives in solid form, which are to be embedded in the enzyme granulates, can be transferred into the process.

In another preferred embodiment, preferably before or especially at the same time as or after step a., as mentioned above or in the following, at the beginning or during the granulation process, instead of enzyme particles other fine-grained up to granular particulate materials (preferred particle size less than 0.5 mm, preferably 0.1-0.2 mm), preferably inert (thus primarily enzymatically inactive) particulate materials can be supplied, e.g., for setting the enzymatic activity of the enzyme granulates, e.g., by inserting correspondingly inert grains, such as inert salt grains, as nuclei material. In this way, the weight percentage of inert grains can equal, e.g., between 0 and 95 wt % of the final enzyme granulate.

As an alternative or a supplement to this embodiment, during the drying and granulation process or during one or more parts of these processes, one or more inert materials, such as, especially salts and/or binding agents, can be supplied not only as grain or nuclei material, but instead for diluting the enzyme or enzymes or especially the (absolute, thus active and inactive enzyme component-bearing) enzyme activity in the matrix of the enzyme granulates (thus distributed within parts or the entire matrix), which represents another especially preferred embodiment of the invention. Here, the inert material or materials can be supplied as solid material, e.g., by registration systems for solid materials, such as 13, within the enzyme solution(s) [=liquid enzyme formulation(s)] (dissolved and/or in suspension), and/or especially in one or more (preferably aqueous) solutions, suspensions, or melts separate from the enzyme solution, especially in the gas streams 2, by means of feeds 26 and/or primarily by means of nozzles, e.g., in the injection zone 22. In the latter case, the solution or suspension or further melts of the inert material or materials (e.g., of a salt, such as inorganic salt of a (e.g., alkali) metallic salt, such as sodium sulfate or common salt, preferably in the presence of a binding agent) by means of one or more separate nozzles in addition to the nozzle or nozzles for spraying the enzyme solution, especially in the region of the gas streams 2, can be sprayed, or advantageously 3 or more material nozzles can be used. In this case, the liquids are given separately into the corresponding nozzle portions and atomized in a favorable embodiment of the invention with similarly supplied (preferably compressed) gas, such as compressed air. The nozzle advantageously has a number of concentric tubes, through which the liquids and the nozzle air are supplied. For example, a first fluid can be supplied through the inner tube, a second fluid through the next outer coaxial annular gap, and the gas for spraying through another coaxial annular gap lying even farther to the outside (a three material nozzle), or a first fluid is supplied through the inner tube, the gas for spraying through a coaxial annular gap to the outer side of the first, a second fluid through another coaxial annular gap lying outside of the last, and additional gas for spraying through a third coaxial annular gap on the outside (a four material nozzle).

This supply of inert material (as nuclei in the core, as an additive in the matrix of the granulate or both) allows, for high relative activity of the used enzyme material (low inactivation), the desired absolute activities (activity for each weight amount of granulate) to be set very precisely and arbitrarily (i.e., between slightly over 0 to 100% of the maximum possible absolute activity), without changing the remaining parameters of the enzyme granulate, like the grain size or the freedom from dust. It can be realized in continuous operation or in batch operation. The percentage of additive to inert material can be 0 to nearly 100%, e.g., from 0.1 to 95 wt %, relative to the solids content of enzyme granulate. The grain size of the inert material can be arbitrary, as long as it is used in a dissolved state; for use as solid powder or as a suspension, the grain size is preferably at 200 μm or less, especially at 100 μm or less.

Thus, the invention also relates to the use of inert materials in the previously and subsequently described method for setting a certain absolute enzyme activity of the enzyme granulates (enzyme activity per (weight) amount of enzyme granulate).

Furthermore, the apparatus can be provided with discharge elements 4 in order to be able to remove particles from the processing space 8. This can be realized, e.g., by an overflow port or by a volumetric discharge element (e.g., a rotary valve) or also by a gravity sifter (e.g., a zigzag sifter charged with sifting gas or a rising pipe separator).

Optionally, mechanical aggregates 27 can be mounted in the processing space 8, but preferably in the region of the return zone 24 at the inclined walls in order to generate through size reduction sufficiently fine material as nuclei for the granulate formation process. Furthermore, the return zone 24 can optionally be used for the position of heating systems or other heat-transfer devices 28. For example, the apparatus wall can be a double-wall in order to use this apparatus for heating or cooling, e.g., under the use of liquid or gaseous heat carriers. Alternatively, microwave heaters could also be used in order to re-dry or preheat the particles in the return zone 24.

In the processing space 8 or in the apparatus parts lying above this space, e.g., in the expansion zone 14 and the discharge air part 19, there can be optional spray nozzles 6, which preferably spray downwards, but also partially upwards. Here, the liquid enzyme formulation can also be injected in order to generate granulation nuclei, e.g., through spray drying in the apparatus. Alternatively, a few of the spray devices 6 and 7 can inject additives or other components in fluid form, which can thus be embedded homogeneously in the granulate structure. If the spray nozzles 7 are adapted to the hot-gas charged supply air chamber 17, optionally the liquid-guiding parts can be provided with insulation or different cooling systems 12 in order to prevent damage to the liquid formulation.

To prevent water susceptibility and/or for controlling the water solubility of the enzyme granulates produced according to the invention, these can be provided with a protective layer through coating in a subsequent, separate process.

As another advantage of the process according to the invention, the very simple construction should be mentioned, which is associated with high operation reliability and flow insensitivity with very good cleaning ability. This creates improved production conditions for exchanging products for biological materials, especially in terms of hygiene requirements.

EXAMPLES

The invention is illustrated with reference to the following concrete application examples without being restricted in any way to these examples.

Example 1

Production of Enzyme Granulates

An enzyme formulation, which contained, in addition to the enzyme solution, a stabilizer as well as binder components, and which had a final concentration of solids of approximately 22 mass percent, was injected into an apparatus, which is characterized by the previously described construction. The processing space is characterized by a rectangular cross section and has above the inclined side walls a cross-sectional area of $0.15 \times 0.2 = 0.03$ m$^2$, and a height of approximately 1 m. The processing gas stream of approximately 180 kg/h heated to approximately 140° C. was supplied by 2 gas supply gaps running longitudinal through the apparatus. The liquid formulation was injected into the processing gas stream with a mass flow of approximately 50 g/min by means of a compressed-air charged dual nozzle spraying vertically upwards. In the processing space there was approximately 500 g of enzyme particles. Through the evaporation process, the processing gas cools and leaves the apparatus at approximately 45° C. The dedusting of the exhaust air was performed by a cyclone connected downstream to the apparatus and the separated solids were supplied by gravity back into the processing space near the gap as nuclei material. The removal of granulates from the processing space was performed at the end under the use of a sieve. The fine portion separated in the sifter was blown pneumatically back into the processing space. The removed granulate has a non-solids bulk density of 800 g/l and the following grain size distribution (sieve analysis):

| | |
|---|---|
| >400 μm: | 0.8 mass % |
| 315-400 μm: | 6.8 mass % |
| 250-315 μm: | 15.3 mass % |
| 160-250 μm: | 42.3 mass % |

-continued

| | |
|---|---|
| 100-160 μm: | 24.9 mass % |
| 0-100 μm: | 9.9 mass % |

Example 2

Enzyme Granulate with Phytase Made from *Aspergillus Niger*

Commercially available phytase (Natuphos 5000 L, BASF, Ludwigshafen, Germany) is diafiltered with demineralized water and an ultra-filtration system with a pore size, which does not let the enzymes pass in order to remove preservatives and salts. The enzymes are then ultra-filtered to obtain a highly concentrated liquid enzyme preparation.

Polyvinyl alcohol as a binding agent is added to 25 wt % of this liquid enzyme preparation with a phytase activity of 24,000 FTU/g and a dry material content of 25 wt %. The remaining 75 wt % of the solution is spray dried at an air inlet temperature of 180° C. and an exhaust air temperature of 70° C. in the apparatus mentioned in Example 1.

The spray-dried enzyme powder is collected in a dust-tight, covered container. It produces an enzyme powder with a phytase activity of 90,000 FTU and 95% dry substance. The container with the spray dried enzyme powder is covered with a dust-tight coupling on the inlet system 13. The liquid enzyme preparation is sprayed with a dosing pump through a spray nozzle into the processing space 8.

Liquid enzyme preparation and enzyme powder are fed in a mass ratio of 4:1. The inlet temperature is at 120° C. and the exhaust air temperature at 60° C. It produces a phytase granulate with the properties shown in Table 1. The content of active and inactive phytase is determined under the use of the procedure described in EP 0 420 356 for characterizing *Aspergillus ficuum* phytase, which is here incorporated by reference.

TABLE 1

Properties of the phytase granulate according to Example 2

| Property | Value |
|---|---|
| Roundness factor | 1.4 |
| Residual moisture | 5% |
| Activity yield | 97% |
| Content of active enzyme/total enzyme content | 95% |
| Activity | 83,000 FTU/g |
| Average grain size D50 | 640 μm |
| Grain size ratio $d_{10}/d_{90}$ | 0.7 |
| Bulk density | 590 g/l |

Example 3

Use of Salt/Binding Solutions

A pilot system with 4 supply chambers and 4 nozzles was used. A protease was used as the enzyme material. Inorganic alkali metallic salts and typical binding agents were used for the salt/binder components. The percentage of components is given in wt % ("%").

a) Pure enzyme solution and salt-binder solution are each fed to different nozzles, the diluted amount of water per nozzle is set to be as equal as possible:

| | | Enzyme solution (cold) | Salt – binder suspension (65° C.) |
|---|---|---|---|
| Chambers | | 3 | 1 |
| Concentration | % | 18 | 50 |
| Spray amount | kg/h | 22 | 12 |
| Water per nozzle | kg/h | 6.0 | 6 |
| Percentage in product | % | 39.8 | 60.2 |
| Feed-air temperature | ° C. | 125 | |
| Discharge-air temperature | ° C. | 55 | | b) Enzyme solution and salt-binder solution are supplied mixed through all nozzles:

| | | Enzyme percentage | Salt + binder percentage |
|---|---|---|---|
| Chambers | | 4 | |
| Percentage in solution | % | 10 | 24 |
| Spray amount | kg/h | 30 | |
| Water per nozzle | kg/h | 4.95 | |
| Percentage in product | % | 29.4 | 70.6 |
| Supply-air temperature | ° C. | 115 | |
| Discharge-air temperature | ° C. | 50 | | c) Enzyme solution and salt-binder solution are supplied separately through three material nozzles:

| | | Enzyme solution (cold) | Salt – binder suspension (65° C.) |
|---|---|---|---|
| Chambers | | 4 | |
| Concentration | % | 15 | 50 |
| Spray amount | kg/h | 15 | 20 |
| Water per nozzle | kg/h | 5.7 | |
| Percentage in product | % | 18.4 | 81.6 |
| Supply-air temperature | ° C. | 120 | |
| Discharge-air temperature | ° C. | 55 | | d) The enzyme-binder solution is sprayed and salt powder is supplied in solid form:

| | | Enzyme – binder solution (cold) | Salt powder <30 μm |
|---|---|---|---|
| Chambers | | 4 | |
| Concentration | % | 15 | 100 |
| Spray amount | kg/h | 20 | 25 |
| Water per nozzle | kg/h | 4.3 | |
| Percentage in product | % | 10.7 | 89.3 |

In conclusion, the following can be stated:

The invention relates to a method for producing enzyme granulates. The object of the invention is to create a method for producing enzyme granulates, for which the enzyme granulates can be produced in continuous or batch wise operation under the prevention as much as possible of non-uniform temperature distributions in the production process and for an increase of the yield of enzyme activity. Simultaneously, the controllability of the granulation for the production should be improved. The enzyme granulate obtained with the method and its use are disclosed.

According to the invention, the enzyme granulates were produced by linking the thermal conditions in the spray zone and the temperature conditions in the remaining region of the fluidized bed. In the process according to the invention, this is achieved such that the heated processing gas for drying is supplied exclusively in the injection region. The reliable supply of particles into the injection region is realized through the special geometrical shape of the apparatus under the use of gravity.

The invention claimed is:

1. Continuous method for producing enzyme granulates comprising:
   a. injecting, in a processing space, one or more fluid enzyme formulations by spraying devices into a heated solids-bearing gas stream,
   b. exposing material particles in the solids-bearing gas stream wetted with liquid in the heated gas stream to a drying and granulation process,
   c. separating the particles from the gas stream after a residence time and feeding the particles back into the processing space by supplying the particles to a gas inlet region by the effect of gravity over inclined surfaces and generating a circular-like solids flow in an axial direction of the processing space through material supply in the gas stream supplied over rotationally symmetric or elongated gap openings,
   d. separating the fine particles, dust, and particles entrained by the processing gas forming the gas stream and feeding them back to the process as nuclei material for the granulation process, supplying the nuclei material into the circular-like solids flow via a range of feeds arranged in a lower region of side walls of the inclined surfaces where the fine particles are suctioned and fed into a zone where the injecting takes place,
   e. removing formed enzyme granulates by the use of discharging elements (4) in the form of sifting devices or volumetric discharge elements and sifting devices, separating enzyme granulates removed from the process that are too large or too small from the material product, processing the enzyme granulates removed from the process that are too large by reducing them in size by a size reduction aggregate and feeding them back into the processing space as nuclei material, and feeding back into the processing space, as nuclei material, enzyme granulates which are removed from the process and which are too small, also supplying these nuclei materials into the circular solids-flow via a range of feeds arranged in the lower region of the inclined surfaces side walls where the fine particles are suctioned and fed into a zone where injection takes place;
   f. keeping an average dwell time of the enzymes in the heated processing space to less than 1.5 hours, and
   g. keeping a grain size distribution of the enzyme granulate to a value, expressed as a ratio of d10/d90, equal to or greater than 0.4.

2. Method according to claim 1, wherein the enzyme granulates fed back into the processing space are heat treated again.

3. Method according to claim 2, wherein the enzyme granulates fed back into the processing space are dried or preheated.

4. Method according to claim 1, wherein the enzyme granulates fed back into the processing space are reduced in size.

5. Method according to claim 1, wherein the enzyme granulates made from different additives and with different mixture ratios are produced.

6. Method according to claim 1, wherein the material particles are exposed to a granulation process after previous spray drying.

7. Method according to claim 1, wherein 5-20 wt %, powdery solid granulate product, obtained by at least one of the process, another source, or at least one enzyme-bearing intermediate product selected from enzyme-bearing powders and dust are supplied to the granulation process.

8. Method according to claim 1, wherein the resulting enzyme granulates are coated with a water-resistant protective film through coating in a subsequent step.

9. Method according to claim 1, wherein before, at the same time or after step a., or during the granulation process, fine-grained up to granular particulate materials selected from one of inert and non-inert particulate materials, are supplied as nuclei material for the drying and granulation process.

10. Method according to claim 1, wherein during the drying and granulation process, or during parts of these processes, one or more inert materials are supplied as grain or nuclei material and/or as additives into the enzyme-granulate matrix or parts of this matrix for diluting the enzyme or enzymes.

11. Method according to claim 10, wherein the inert material or materials are supplied as solid material within the enzyme solution and/or into one or more solutions, suspensions, or melts separate from the enzyme solution.

12. Method according to claim 10, wherein one or more solutions and/or suspensions of the inert material or materials are sprayed by one or more separate nozzles in addition to one or more nozzles for the spraying of the liquid enzyme formulation during the drying and granulation process, or during parts of these processes.

13. Method according to claim 10, wherein one or more multi-material nozzles and a gas for atomizing one or more solutions or suspensions of one or more inert materials are used.

14. Method according to claim 1, wherein enzyme granulates are produced having a compression strength of 10 MPa or higher.

15. Method according to claim 1, wherein enzyme granulates are produced having a dust content according to the Heubach test of lower than 800 ppm.

16. Method according to claim 1, wherein the removal of the granulates is performed using a sieve.

17. Method according to claim 1, wherein the axial solids flow is generated around a horizontally axial direction of the processing space.

* * * * *